United States Patent [19]

Halvorsen

[11] 4,252,122
[45] Feb. 24, 1981

[54] FITTING ASSEMBLY FOR GUIDING AND RETAINING A PROBE IN A CATHETER

[75] Inventor: Kenneth Halvorsen, Huntington Beach, Calif.

[73] Assignee: Medical Testing Systems, Inc., Fountain Valley, Calif.

[21] Appl. No.: 37,696

[22] Filed: May 10, 1979

[51] Int. Cl.³ .......................................... A61M 25/00
[52] U.S. Cl. .............................................. 128/349 R
[58] Field of Search ............... 128/349 R, 348, 350 R, 128/274, 247, 214.4, DIG. 9, 214 R; 279/1 R, 1 A, 1 N, 7

[56] References Cited

U.S. PATENT DOCUMENTS

| 3,241,554 | 3/1966 | Coanda | 128/350 R |
| 3,859,985 | 1/1975 | Eckhart | 128/274 |
| 4,159,022 | 6/1979 | Pevsner | 128/214.4 |

*Primary Examiner*—John D. Yasko
*Attorney, Agent, or Firm*—Edward H. Loveman

[57] ABSTRACT

A fitting assembly for guiding and retaining a probe in a catheter, comprises a generally cylindrical housing in which is a tubular body through which a probe can pass. Inside one end of the housing is a tubular resilient gasket which bears on one end of the tubular body. An internally threaded cap is engaged on a threaded nipple at one end of the housing and is movable axially upon rotation to compress the gasket and hold the probe in place. An internal projection in the cap engages on an annular shoulder on the housing to keep the cap from being detached from the assembly. A nipple at the other end of the tubular body engages a threaded fitting at one end of the catheter. An adapter coupling is provided having an internally threaded end engageable on the threaded fitting at the end of the tubular body, and having an internally threaded other end in which is engageable an externally threaded fitting of a catheter provided with such a fitting.

8 Claims, 7 Drawing Figures

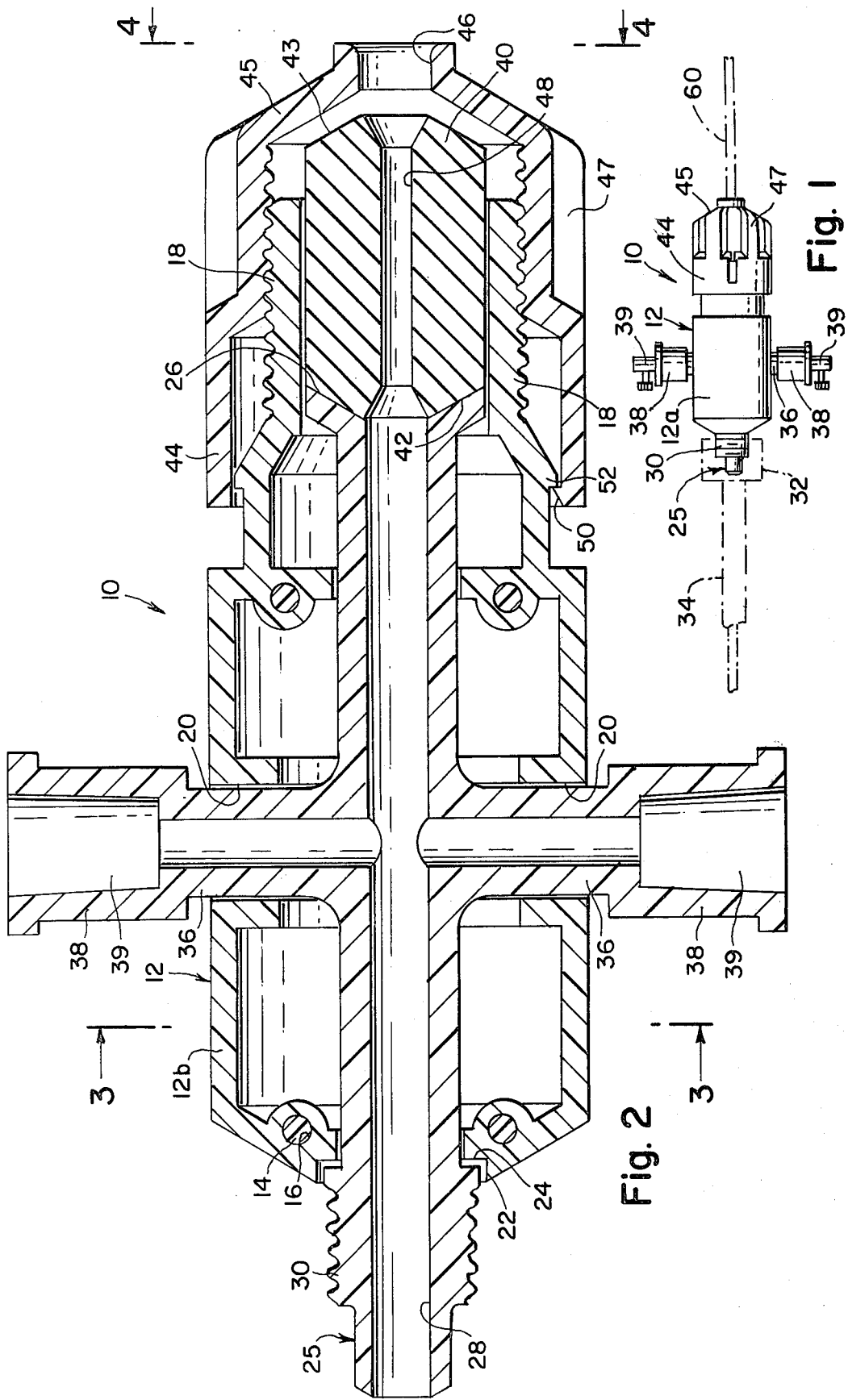

FITTING ASSEMBLY FOR GUIDING AND RETAINING A PROBE IN A CATHETER

This invention concerns a fitting for mechanically guiding sealing and retaining a probe in a catheter, and adapted to release the probe to permit axial movement of the probe in the catheter.

Fittings of various types have been known heretofore which were adapted to engage on one end of a flexible catheter, to facilitate and guide insertion of a flexible probe into the catheter.

The present invention involves a fitting comprising an assembly which involves several improvements over the prior known probe guides for catheters. The present assembly may be made entirely of transparent plastic material, and is relatively inexpensive so that it may be discarded after a single use. It will accomodate lateral valves by means of which dye or drugs may be injected into a patient, the patient's blood pressure taken and for other uses. The fitting has a generally cylindrical housing in which is a compressible tubular gasket through which the probe may be inserted at one end of the fitting into a catheter engaged at the other end of the fitting. A cylindrical nut screws on the catheter and adjustably compresses the gasket to lock the probe in place. The nut has a lip which engages a shoulder on the fitting housing to keep the nut from disengaging from the housing. The fitting has a body terminating in an external threaded portion on which an internally on which an internally threaded fitting at the end of the catheter can be engaged. An adapter coupling is provided for mounting of an externally threaded fitting. This adapter terminates in a female fitting which may engage a male fitting at the end of a catheter equipped with this type of fitting. All parts of the fitting assembly may be molded of plastic parts which are relatively inexpensive.

It is therefore a principal object of the present invention to provide a fitting for mechanically guiding, sealing, and coupling a probe to a catheter.

Another object of the present invention is to provide a fitting of the type described which is adapted to release the probe to permit axial movement thereof in the catheter without disturbing the seal.

These and other objects and many of the attendant advantages of this invention will be readily appreciated as the same becomes better understood by a reference to the following detailed description when considered in connection with the accompanying drawings in which:

FIG. 1 is a side elevational view of a fitting embodying the present invention;

FIG. 2 is an axial sectional view of the assembly on an enlarged scale;

Figure 3:
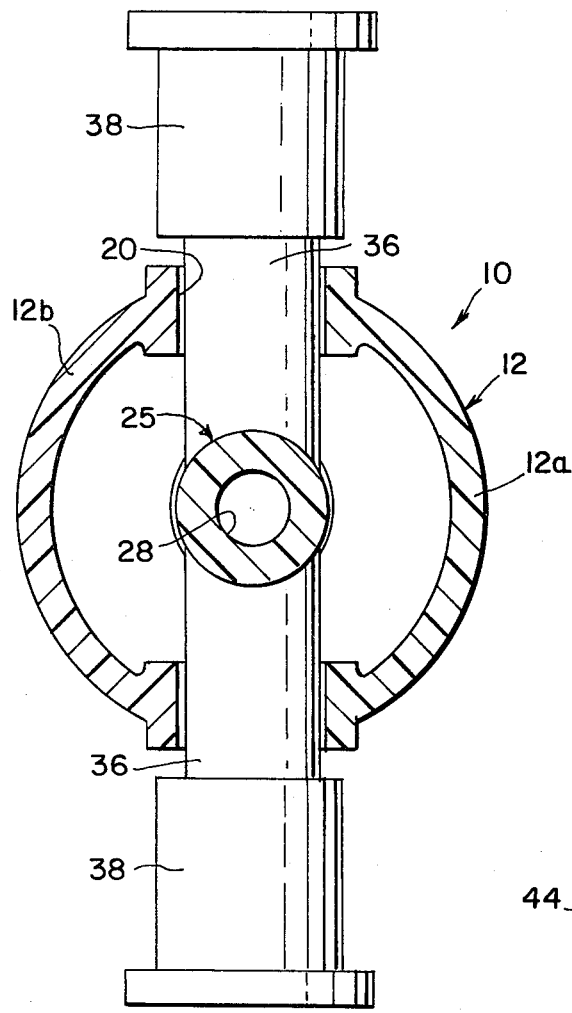
FIG. 3 is a cross sectional view taken along line 3—3 of FIG. 2.
Figure 4:
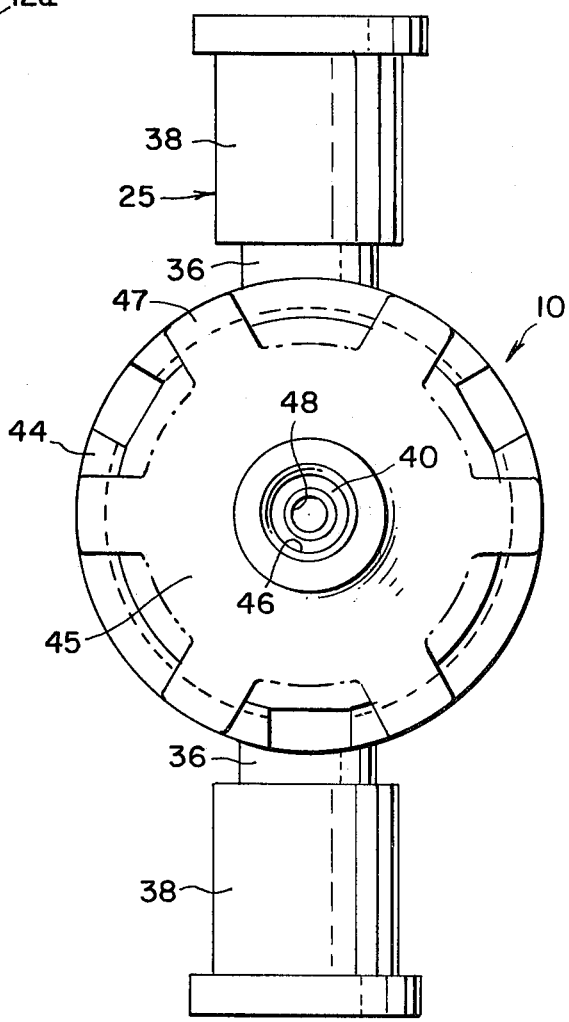
FIG. 4 is an end elevational view taken along line 4—4 of FIG. 2.
Figure 5:
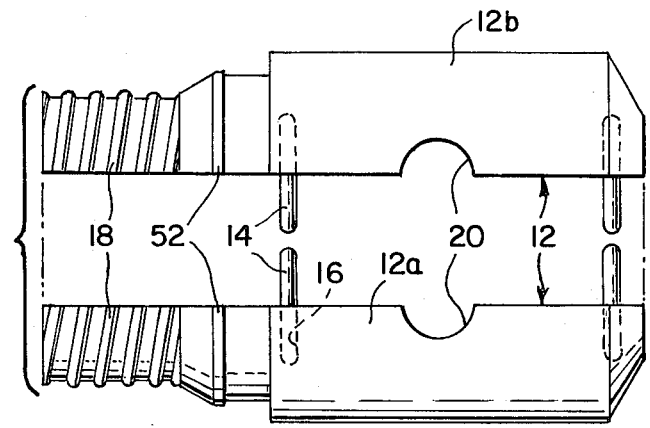
FIG. 5 is an exploded side elevational view showing parts of the assembly housing.

Referring now to the drawings wherein like reference characters designate like or corresponding parts throughout, there is illustrated in FIGS. 1-4 a fitting or a fitting assembly generally designated as reference numeral 10 having a generally cylindrical housing 12 made up of two similar semicylindrical parts 12a, 12b. Each part 12a and 12b, has a pair of projecting pins 14 which fit into corresponding recesses 16 in the other part to form the complete housing 12; see FIG. 5. The housing 12 has an externally threaded nipple 18 at one end. Two lateral diametrically opposed openings 20 in the housing 12 open into the interior of the housing 12. The housing 12 terminates at the other end on an opening 22 having an internal annular shoulder 24.

The fitting assembly 10 has an elongated tubular body 25 extending through the housing 12. The body 25 terminates at one end in a conical recess or seat 26. A bore 28 extends through the body 25. At the other end of the fitting body 25 is an externally threaded nipple 30 on which can engage an internally threaded fitting 32 of a catheter 34; see FIG. 1. The body 25 has two laterally extending tubular arms or branches 36 each of which terminates in a cup 38 to receive a valve 39. The valves 39 are normally closed but may be opened for injecting fluid into the body bore 28 or for other purposes. Housing parts 12a, 12b may be cemented together after insertion of the fitting body 25 in the housing 12.

A tubular resilient gasket 40 with conical end faces 42, 43 fits into the seat 26 inside the nipple 18 of the fitting housing 12. The gasket 40 projects axially out of the nipple 18 as clearly shown in FIG. 2. An internally threaded cup 44 engages on the nipple 18. The cap 44 has an apertured end wall 45 with an opening 46 aligned with a bore 48 in the gasket 40 and with the bore 28 in the body 25. The end wall 45 is conical, and can engage the tapered or conical end face 43 of the gasket 40 when the cap 44 is threaded fully on the nipple 18. A radially extending lip 50 is formed at the inside other end of the cap 44. When the cap 44 is threaded on the nipple 18 (to the left as viewed in FIG. 2), the lip 50 snaps over a radial annular shoulder 52, on the outside of the housing 12. This engagement of the lip 50 on the shoulder 52 serves as a locking means to trap and prevent unthreading of the cap 44 fully from the housing 12. However, the cap 44 can be threaded further to the left axially of the housing 12 to compress the gasket 40. Ridges 47 on the cap 44 facilitate turning the cap 44. A wire probe 60 (shown in FIG. 1) may be inserted axially through the end of the wall 45 of the cap 44, then through the gasket 40, the body 25, and through the catheter 34. The probe 60 can be moved freely when the cap 44 is loosened to the position shown in FIG. 2. When the cap 44 is tightened by rotation to move it axially to the left on the nipple 18, the gasket 40 will be compressed and will grip the probe 60 securely holding it in place and preventing further axial movement. To retract the probe 60, or to change its position axially of the catheter 34, the cap 44 will be turned to loosen it to the position shown in FIG. 2, where the gasket 40 expands to release the probe 60.

Figure 6:
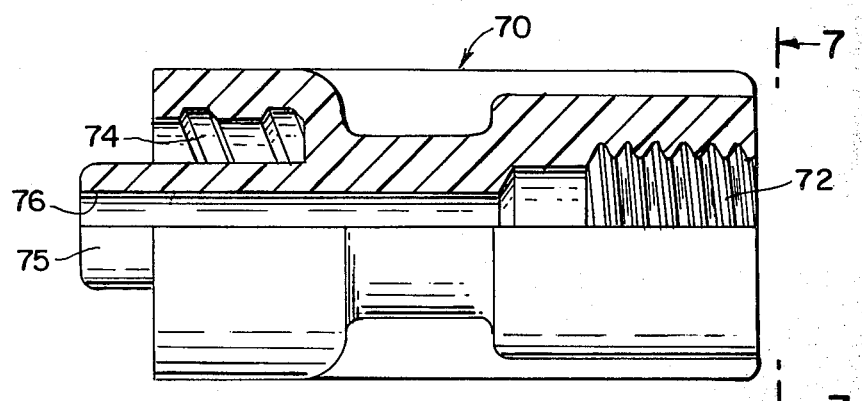
FIG. 6 is a side elevational view partially in section of an adapter coupling for a catheter.
Figure 7:
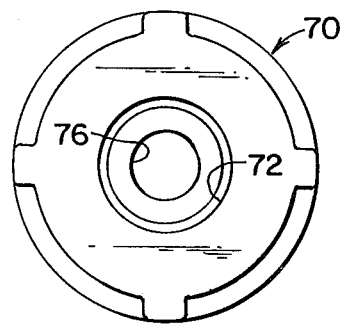
FIG. 7 is an end elevational view taken along line 7—7 of FIG. 6.

FIGS. 6 and 7 show an adapted coupling 70 comprising a cylindrical member having an internally threaded recess 72 at one end which engages on the externally threaded nipple 30 of the body 25. The other end of the coupling 70 terminates in an internally threaded seat 74 which may receive an externally threaded fitting (not shown) at the end of a catheter provided with such a fitting. A nipple 75 at the end of the coupling 70 aligns axially with the catheter. A bore 76 in the coupling 70 aligns with the bore 28 in the body 25 of the fitting assembly 10.

All parts of the fitting assembly 10 including coupling 70 are preferably made of transparent plastic material such as clear polycarbonate. They may be mass produced by molding machinery at relatively low cost, and may be discarded after a single usage.

The fitting assembly 10 may be a rather small device about 2¼ inches in length overall and about 1¼ inches in maximum width. The total axial travel of the cap 44 after engagement of the lip 50 on the shoulder 52 need be only about 0.1 of an inch, but this will be sufficient to compress the gasket 40 to engage the probe 60 and hold it in place.

It should be understood that the foregoing relates to only a preferred embodiment of the invention, and that it is intended to cover all changes and modifications of the example of the invention herein chosen for the purposes of the disclosure, which do not constitute departures from the spirit and scope of the invention.

What is claimed is:

1. A fitting assembly for guiding, sealing, and releasably holding a probe in a catheter comprising:
   a generally cylindrical hollow housing, one end thereof having an externally threaded nipple, and a radial annular shoulder adjacent to said nipple;
   a tubular body extending through said housing and having a bore extending therethrough for receiving an elongated probe;
   a resilient tubular gasket seated in said end of said housing bearing at one end against an adjacent end of said tubular body; and
   a cap internally threaded to engage on said threaded nipple of said housing, said cap being formed with a radially extending projection engageable on said shoulder to prevent said cap from axially detaching from said nipple while permitting axial movement of said cap to compress said gasket and thereby guide, seal and releasably hold said probe in place on said body.

2. A fitting assembly as defined in claim 1, wherein said body has means at its other end for engaging an end of said catheter thereon in axial alignment with said bore to receive said probe.

3. A fitting assembly as defined in claim 2, wherein said body has at least one tubular arm extending radially through an aperture in said housing to provide communication with said bore in said body.

4. A fitting assembly as defined in claim 3, wherein said arm has internal recess adapted to receive a valve for controlling communication with said bore in said body.

5. A fitting assembly as defined in claim 4, wherein said housing is formed of two complementary generally semicylindrical mating parts for enclosing said body.

6. A fitting assembly as defined in claim 5, wherein said means at said other end of said body is an externally threaded other nipple adapted to engage an internally threaded fitting at one end of said catheter.

7. A fitting assembly as defined in claim 6, futher comprising a generally cylindrical adapter coupling having an internally threaded recess at one end adapted to engage on said other nipple at said other end of said body, said coupling having another internally threaded recess at its other end for engaging an externally threaded fitting at one end of said catheter provided with such a fitting.

8. A fitting assembly as defined in claim 7, wherein substantially all parts of said assembly are formed of transparent plastic material.

* * * * *